(12) United States Patent
Lehmann et al.

(10) Patent No.: US 9,170,250 B2
(45) Date of Patent: Oct. 27, 2015

(54) OILFIELD CHEMICALS WITH ATTACHED SPIN PROBES

(71) Applicant: Baker Hughes Incorporated, Houston, TX (US)

(72) Inventors: Marc N. Lehmann, Houston, TX (US); Matthew Hilfiger, Richmand, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 304 days.

(21) Appl. No.: 13/785,407

(22) Filed: Mar. 5, 2013

(65) Prior Publication Data

US 2013/0236983 A1    Sep. 12, 2013

Related U.S. Application Data

(60) Provisional application No. 61/609,617, filed on Mar. 12, 2012.

(51) Int. Cl.
*G01N 24/00* (2006.01)
*G01N 33/28* (2006.01)

(52) U.S. Cl.
CPC ........... *G01N 33/2823* (2013.01); *Y10T 436/24* (2015.01)

(58) Field of Classification Search
None
See application file for complete search history.

(56) References Cited

U.S. PATENT DOCUMENTS

| 4,317,735 | A | 3/1982 | Crowe | |
|---|---|---|---|---|
| 4,560,663 | A * | 12/1985 | Nicksic et al. | 436/25 |
| 6,464,009 | B2 | 10/2002 | Bland et al. | |
| 7,205,762 | B2 * | 4/2007 | Blanz et al. | 324/303 |
| 2008/0108519 | A1 | 5/2008 | Harris et al. | |
| 2010/0147065 | A1 | 6/2010 | Tan et al. | |
| 2011/0067867 | A1 | 3/2011 | Reddy et al. | |

OTHER PUBLICATIONS

Kim, Y. et al. Molecular Motions and Ordering of the Interfacial, Droplet and Binder Regions of Polymer-Dispersed Liquid-Crystal Displays—A Paramagnetic-Resonance Spin-Probe Study, 1995, J. Appl. Phys. vol. 77(5), pp. 1914-1922.*

* cited by examiner

*Primary Examiner* — Robert Xu
(74) *Attorney, Agent, or Firm* — Mossman Kumar & Tyler PC

(57) ABSTRACT

Detecting a spin probe in an oilfield fluid may indicate or determine the amount of the particular chemicals within an oilfield fluid. The detection of the spin probe may also indicate at least one property of the oilfield fluid, such as but not limited to pH, dielectric constant, rotational freedom of the spin probe, at least one chemical, the concentration of at least one chemical, residue of at least one chemical in the fluid, the speciation of coupled chemistry between the spin probe and the chemical, and combinations thereof. In one non-limiting embodiment, the spin probe may be attached to at least one chemical. The oilfield fluid may be or include, but is not limited to, a drilling fluid, a completion fluid, a production fluid, a servicing fluid, and combinations thereof.

10 Claims, No Drawings

OILFIELD CHEMICALS WITH ATTACHED SPIN PROBES

CROSS-REFERENCE TO RELATED APPLICATION

This application claims the benefit of Provisional Patent Application No. 61/609617 filed Mar. 12, 2012, which is incorporated by reference herein in its entirety.

TECHNICAL FIELD

The present invention relates to methods and compositions for detecting the presence and/or quantity of oilfield chemicals, and more particularly relates to detecting spin probes within an oilfield fluid for identifying at least one property of the oilfield fluid.

BACKGROUND

The drilling and production of a hydrocarbon reservoir requires the use of several types of oilfield fluids, such as but not limited to drilling fluids, completion fluids, production fluids, servicing fluids, and combinations thereof.

Drilling fluids are used in operations to drill boreholes into the earth; 'drilling fluid' is typically synonymous with 'drilling mud'. One classification of drilling fluid is based on the composition of the fluid or mud. For example, water-based fluids, brine-based fluids, oil-based fluids and synthetic-based fluids, which are synthetically produced rather than refined from naturally-occurring materials.

Completion fluids are used to "complete" an oil or gas well for facilitating final operations prior to initiation of production, such as setting screens production liners, packers, downhole valves or shooting perforations into the producing zone. The fluid may help to control a well should downhole hardware fail, without damaging the producing formation or completion components. Completion fluids are typically brines (chlorides, bromides and formates), as long as the fluid is of proper density and flow characteristics. The fluid should be chemically compatible with the reservoir formation and fluids, and is typically filtered to a high degree to avoid introducing solids to the near-wellbore area. A regular drilling fluid is typically not suitable for completion operations because of their solids content, pH and ionic composition; however, drilling fluids may occasionally be suitable for both purposes.

Production fluid is the fluid that flows from a formation to the surface of an oil well. These fluids may include oil, gas, water, as well as any contaminants (e.g. H2S, asphaltenes, etc.). The consistency and composition of the production fluid may vary.

Servicing fluids, such as remediation fluids, workover fluids, and the like, have several functions and characteristics necessary for repairing a damaged well. Such fluids may be used for breaking emulsions already formed and for removing formation damage that may have occurred during the drilling, completion and/or production operations. The terms "remedial operations" and "remediate" are defined herein to include a lowering of the viscosity of gel damage and/or the partial or complete removal of damage of any type from a subterranean formation. Similarly, the term "remediation fluid" is defined herein to include any fluid that may be useful in remedial operations. These servicing fluids aid in balancing the pressure of the reservoir and prevent the influx of any reservoir fluids.

It is often beneficial to detect chemicals added to these fluids to monitor or determine a property of the oilfield fluid and/or the wellbore. These types of fluids may also be used to perform squeeze techniques where it is beneficial to force a treatment fluid or slurry into a planned treatment zone for further monitoring or detection of various properties. Such properties that may be monitored or detected may include, but are not limited to pH, dielectric constant, a chemical, an absorbance or emission at a given wavelength or integrals of wavelengths, magnetic property, and combinations thereof.

For example, determining the amount of the asphaltene inhibitors returning from a wellbore "squeeze" allows for determination of the "squeeze" lifetime and thus may act as a protection margin for the well against potential asphaltene deposition. The same is true for determining the use and/or amount of paraffin inhibitors, scale inhibitors, corrosion inhibitors, biocides, hydrogen sulfide scavengers, demulsifiers, reverse emulsion breakers, water clarifiers, drag reducers, and combinations thereof. Examples of suitable scale inhibitors may include, but are not limited to phosphinates, sulfonated polymers and copolymers, acrylic acid polymers and copolymers, phosphate esters, and the like.

Detecting these types of chemicals is often difficult because of the complexity of detecting such chemicals added to organic fluids or matrices with similar properties. That is, it is sometimes difficult to differentiate between added oilfield fluids.

It would be desirable if methods and compositions could be devised to better detect the presence, amounts and/or properties of the oilfield fluids and/or added chemicals typically used within the aforementioned fluids.

SUMMARY

There is provided, in one form, a method for detecting at least one spin probe within its microenvironment of an oilfield fluid. The presence of the spin probe may indicate the presence of at least one chemical, pH of the microenvironment, dielectric constant of the microenvironment, rotational freedom of the spin probe, the concentration of the chemical(s), residue of the chemical(s) in the fluid, the speciation of the coupled chemistry between the spin probe and the chemical(s), the placement origin of the chemical(s), secondary phenomena of the microenvironment, and combinations thereof. The oilfield fluid may be or include, but is not limited to, a drilling fluid, a completion fluid, a production fluid, a servicing fluid, and combinations thereof. The chemical may be, but is not limited to an oil-based chemical, a water-based chemical, and combinations thereof.

There is further provided in another non-limiting embodiment a method for probing at least one property of an oilfield fluid for at least one chemical. Spin probes with at least one chemical attached may indicate at least one property, such as but not limited to, the presence of at least one chemical, pH, dielectric constant, rotational freedom of the spin probe, the concentration of at least one chemical, residue of at least one chemical in the fluid, the speciation of the coupled chemistry between the spin probe and the chemical, the placement origin of the chemical, and combinations thereof. The placement origin of the chemical may indicate secondary phenomena, such as but not limited to the occurrence of water breakthrough (e.g. seawater, aquifer water, produced water, and the like) within a production zone, between wells, and the like; commingling of produced fluids in well tubing, flow line manifolds and pipeline networks; instantaneous water cut, fluid viscosities, multiphase viscosities, and the like. The spin probe may be integrated into the methods or monitoring techniques of controlling wells with neural networks. Moreover, the spin probe may be used to assess deposition of wax inhibitors or polymer systems, waxes, asphaltenes, scale and/or naphthenates within the wellbores, tubing manifold, flowlines, etc. The oilfield fluid may be or include a drilling fluid, a completion fluid, a production fluid, a servicing fluid, and combinations thereof. The chemical may be, but is not limited to, an oil-based chemical, a water-based chemical, and combinations thereof.

In another form, a fluid composition is provided that may include an oilfield fluid, at least one spin probe, and at least one chemical. The chemical may be or include, but is not limited to asphaltene inhibitors, paraffin inhibitors, scale inhibitors, corrosion inhibitors, biocides, low dose hydrate inhibitors, oxygen scavengers, hydrogen sulfide scavengers, demulsifiers, reverse emulsion breakers, water clarifiers, drag reducers, foamers, defoamers, fracturing fluid additives, water flooding additives, carbon dioxide flooding additives, and combinations thereof. The oilfield fluid may be or include, but is not limited to a drilling fluid, a completion fluid, a production fluid, a servicing fluid, and combinations thereof.

The detection of the spin probes may indicate the presence and/or amount of either the spin probe and/or the chemical(s) within the oilfield fluid, the wellbore, a pipeline, a refinery, and the like.

DETAILED DESCRIPTION

It has been discovered that spin probes may be added as a component within an oilfield fluid for detection of at least one property, such as, but not limited to, the presence of at least one chemical, pH, dielectric constant, rotational freedom of the spin probe, the concentration of at least one chemical, residue of at least one chemical in the fluid, the speciation of the coupled chemistry between the spin probe and the chemical, the placement origin of the chemical, and combinations thereof. A 'spin probe' is defined herein to be a molecule or ion having a stable unpaired electron or otherwise stable free radical character that may or may not also carry a functional group. The spin probe may be added to the oilfield fluid alone, or it may be coupled to another molecule, such as a chemical.

The spin probe may allow for determining the presence, the amount and/or the properties of either the spin probe and/or an attached chemical within a microenvironment surrounding the spin probe. 'Microenvironment' is defined herein to include the surrounding environment relative to the spin probe, such as but not limited to the oilfield fluid, the wellbore, a pipeline, a refinery, and the like. The placement origin of the chemical may indicate secondary phenomena, such as but not limited, to the occurrence of water breakthrough within a production zone, or between wells, and the like.

Once detected, the spin probe may indicate the concentration of a particular chemical and/or identify the chemistry being applied if more than one spin probe is utilized in a particular location or zone. In a non-limiting embodiment, two or more types of spin probes may be used within the same oilfield fluid for detection and/or identification of two or more properties. In addition, the detection of the spin probe and its coupled chemistry may be used to ascertain which zone is being produced, or to determine whether water breakthrough is occurring from a producing zone when the spin probe is associated with a specific phase. For example, the spin probe and its associated chemistry may be adsorbed or retained within a proppant matrix or proppant additive to be incorporated into a fracture or sandpack to determine the concentration of the spin probe and/or to ascertain the level of depletion of a chemical from the matrix and the release rate. In another non-limiting example, a detected spin probe may aid in determining the lifetime of a chemical treatment. The listed treatment options may be used alone or in combination by using same or different spin probes to aid resolution of the origin of the spin probe and its associated chemistry.

The spin probe within the oilfield fluid may range from about 10 ppm independently to about 50,000 ppm for detection of the spin probe, or alternatively from about 100 ppm independently to about 25,000 ppm, or from about 1,000 ppm independently to about 10,000 ppm in another non-limiting embodiment. The spin probe may have a g value ranging from about 1.4 independently to about 3.0 in one non-limiting embodiment, or from about 2.000 independently to about 2.100 in an alternative embodiment.

In another non-limiting embodiment, the spin probe may be an organic radical having a g value ranging from about 1.4 independently to about 3.0, alternatively from about 1.99 independently to about 2.01. "Organic radical" as used herein refers to a type of radical having at least one carbon atom, e.g. triphenylmethyl radical. "Independently" as used herein means that any lower threshold may be combined with any upper threshold to define an acceptable alternative range.

The spin probe may be or include, but is not limited to [(2,2,6,6-tetramethylpiperidin-1-yl)oxyl] (TEMPO), [2,2,5,5-tetramethylpyrrolidin-1-yloxyl] (Proxyl), [2,2,5,5-tetramethyl-3-oxazolidinoxy] (Doxo), [2,2,5,5tetramethyl-1-dihydropyrrolinoxy] (Proxo), [2,2,3,4,5,5-hexamethyl-imidazoline-1yloxyl] (Imidazo), [2,5-dihydro-3-(hydroxymethyl)-2,2,5,5-tetramethyl-1H-pyrrol-1-yloxy], [5-(Diethoxyphosphoryl)-5-methyl-1-pyrroline-N-oxide] (DEPMPO), [5-(Diisopropoxyphosphoryl)-5-methyl-1-pyrroline-N-oxide], [2-Diisopropylphosphono-2-methyl-3,4-dihydro-2H-pyrrole-1-oxide] (DIPPMPO), [5-tert-Butoxycarbonyl-5-methyl-1-pyrroline-N-oxide] (BMPO), [5,5-Dimethyl-1-pyrroline-N-oxide] (DMPO), [2-Ethoxycarbonyl-2-methyl-3,4-dihydro-2H-pyrrole-1-oxide] (EMPO), [4-Hydroxy-5,5-dimethyl-2-trifluoromethylpyrroline-1-oxide] (FDMPO), [bis-(2,2,5,5-Tetramethyl-3-imidazoline-1-oxyl-4-yl) disulfide, biradical] (RSSR), [4-(Dimethylamino)-2-ethyl-5,5-dimethyl-2-pyridine-4-yl-2,5-dihydro-1H-imidazol-1-oxyl] (DEDPI), [(1-Oxyl-2,2,5,5-tetramethylpyrroline-3-methyl)] methanethiosulfonate (MTSSL), [2-n-Heptyl-4-hydroxyquinoline N-oxide] (HQNO), [N-t-Butyl-α-phenylnitrone] (PBN), [N-(Dithiocarbamoyl)-N-methyl-D-glucamine (MGD. Na .H2O)], Diethyldithiocarbamate, [2-(4-Carboxyphenyl)-4,4,5,5-tetramethylimidazoline-1-oxyl-3-oxide. potassium salt] (Carboxy-PTIO . K), and combinations thereof.

Alternatively, the spin probe may be or include a metal ion, such as but not limited to transition metal ions, lanthanides metal ions, rare earth metals (e.g. gadolinium), and combinations thereof; as well as salts or complexes of these transition metal ions that may be formed as microparticles or nanoparticles, such as quantum dots in one non-limiting example. Or in another non-limiting embodiment, the spin probe may be, but is not limited to copper, vanadium, manganese, iron, and combinations thereof. These metal ions may have unpaired spins in their electronic structures for use as spin probes. The g-value for metal ions may range from about 1.4 independently to about 3 depending on the geometry of the metal ion or metal complex ion, or alternatively from about 1.8 independently to about 2.4. The g value may vary because of the spin-orbit coupling and/or zero field splitting. For example, the g-value of copper acetylacetonate $(Cu(acac)_2)$ is 2.13.

The steric hindrance around a particular functional group or unpaired electron within the spin probe may be responsible for the stability of the spin probe. The functional group may include a nitroxide group, a branched or unbranched $C_1$-$C_{30}$ alkyl chain group, an aromatic or phenyl group, and combinations thereof. In one non-limiting embodiment, the biostability of a few of the spin probes having nitroxide groups may be ranked where Proxo and Imidazo have a similar biostability, but both may have a greater biostability than Doxo, which has a higher stability than Tempo (e.g. Imidazo≈Proxo>>Doxo>Tempo).

The detection of the spin probe within an oilfield fluid may also detect and/or determine an attached chemical. Attaching of the spin probe to a chemical may occur prior to the addition of the spin probe to the oilfield fluid. Alternatively, the spin probes may attach to the chemical(s) after both are added to the oilfield fluid. The spin probe may be attached to the chemical of interest by a reaction. For example, HTEMPO may react directly with a carboxcylic acid derivative to form an ester. In a non-limiting embodiment, the spin probe may be modified, e.g. HTEMPO may react with epichlorohydrin or acid chlorides to create a spin probe capable of having functional groups attached thereto, such as but not limited to alcohols and amines.

The chemical may be an oil-based chemical, a water-based chemical, and combinations thereof. The attachment of the spin probe to the chemical may be a covalent attachment via a reaction, such as but not limited to esterification, nucleophilic addition, substitution, elimination, rearrangement, and combinations thereof. In an alternative embodiment, the chemical may be, but is not limited to asphaltene inhibitors, paraffin inhibitors, scale inhibitors, corrosion inhibitors, biocides, low dose hydrate inhibitors, oxygen scavengers, hydrogen sulfide scavengers, demulsifiers, reverse emulsion breakers, water clarifiers, drag reducers, foamers, defoamers, fracturing fluid additives, water flooding additives, carbon dioxide flooding additives, and combinations thereof.

Examples of the fracturing fluid additives may include, but are not limited to gellants, gel breakers, crosslinkers, and combinations thereof. Other chemicals may include additives typically used for water flooding, alkaline surfactant polymer (ASP) floods, $CO_2$ floods, and/or other enhanced oil recovery (EOR) techniques. It would be obvious to one skilled in the art as to which chemicals listed above may be coupled with a spin probe to be utilized in downstream and midstream operations.

The spin probe may be coupled to a scale inhibitor in one non-limiting embodiment, which aids in preventing scale deposition within or on the wellbore, which reduces the amount of scale within production fluids (e.g. produced water) or during water-flooding operations. In another non-limiting embodiment, the spin probe may be coupled to a paraffin or asphaltene inhibitor where the spin probe may be returned after production for monitoring the presence or concentration of paraffins or asphaltene inhibitors. Monitoring these inhibitors allows for one to maintain the concentrations of the inhibitors at minimum effective concentrations to provide flow assurance and avoid blockages related to excess paraffin or asphaltene deposits.

In one non-limiting embodiment, the device that may detect the spin probe may be, but is not limited to, an electronic paramagnetic resonance (EPR) instrument by tuning the EPR to a particular g value for detection of the desired spin probe. A calibration curve may be generated for the spin probe within a desired oilfield fluid to determine the concentration of the spin probe with attached chemicals within the oilfield fluid. The detection of the spin probes by an EPR is not impacted by matrix quenching, i.e. where paramagnetic species are destroyed or removed by mechanisms through which singlet or triplet states are quenched by reaction or recombination of other paramagnetic species, such as nitroxides. This is beneficial when the use of an EPR is compared to detection devices using fluorescent techniques, which may be adversely affected by matrix quenching.

The oilfield fluid may be a drilling fluid, a completion fluid, a production fluid, or a stimulation fluid. The oilfield fluid may be a non-aqueous fluid or an aqueous fluid, or the oilfield fluid may be a single-phase fluid, or a poly-phase fluid, such as an emulsion of oil-in-water (O/W) or water-in-oil (W/O). The amount of the chemical within the oilfield fluid may range from about 10 ppm independently to about 20,000 ppm for detection of the chemical, or alternatively from about 50 ppm independently to about 5,000 ppm, or from about 100 ppm to about 1,000 ppm in another non-limiting embodiment.

The concentration of the spin probe(s) within the oilfield fluid may range from about 10 ppm independently to about 50,000 ppm, alternatively from about 100 ppm independently to about 10,000 ppm. The spin probes may be added to the oilfield fluid followed by the addition of the chemicals to the oilfield fluid, or the spin probe may be pre-attached to the chemical for subsequent addition of the spin probe and attached chemical. An optional surfactant may be used to improve the quality of the dispersion of the spin probes and/or the chemicals within the oilfield fluid and may also enhance the thermodynamic, physical, and rheological properties of these types of fluids. Such surfactants may be present in the oilfield fluid in an amount ranging from about 10 ppm independently to about 500 ppm, alternatively from about 200 ppm independently to about 3000 ppm.

Spin probes may be attached to the surfactants, polymers, or other chemicals typically used for purposes of water-flooding, $CO_2$ flooding, and/or other EOR techniques. Enhanced oil recovery describes a general set of injection processes using special chemical solutions for purposes of enhancing oil recovery. Micellar, alkaline, soap-like substances, and the like may be used to reduce surface tension between oil and water in the reservoir, whereas polymers such as polyacrylamide or polysaccharide may be employed to improve sweep efficiency, which is a measure of the effectiveness of an EOR that depends on the volume of the reservoir contacted by the injected fluid. The chemical solutions may be pumped through specially distributed injection wells to mobilize oil left behind after primary or secondary recovery.

Chemical flooding is a major component of enhanced oil recovery processes and may be subdivided into micellar-polymer flooding and alkaline flooding. The general procedure of a chemical flood may include a preflush (low-salinity water), a chemical solution (micellar or alkaline), a mobility buffer and, finally, a driving fluid (water), which displaces the chemicals and the resulting oil bank to production wells. The pre-flush and the mobility buffer are optional fluids.

Water flooding may be performed by injected water into the reservoir formation to displace residual oil adjacent to production wells. When performing a water-flooding process, a surfactant may increase the viscosity of the water closer to that of oil, so that less bypassing or channeling of the flood water may occur. Said differently, the mobility of the flood water may be decreased to provide a greater displacement of the flood front.

Such water-flooding techniques may include the alkaline surfactant polymer (ASP) technique, where a very low concentration of the surfactant may be used to create a low interfacial tension between the trapped oil and the injection fluid/formation water. The alkali present in the injection fluid may then be able to penetrate deeper into the formation and contact the trapped oil globules. The alkali may react with the acidic components of the crude oil to form additional surfactant in-situ, thus, continuously providing ultra low interfacial tension and freeing the trapped oil. With the ASP technique, surfactant may be used to increase the viscosity of the injection fluid, to minimize channeling, and provide mobility control. Carbon dioxide ($CO_2$) flooding is similar to water flooding, except that carbon dioxide is injected into an oil reservoir instead of water in order to increase the extraction of oil from a reservoir.

Expected suitable surfactants may include, but are not necessarily limited to non-ionic, anionic, cationic, amphoteric surfactants and zwitterionic surfactants, janus surfactants, and blends thereof. Suitable nonionic surfactants may include, but are not necessarily limited to, alkyl polyglycosides, sorbitan esters, methyl glucoside esters, amine ethoxylates, diamine ethoxylates, polyglycerol esters, alkyl ethoxylates, alcohols that have been polypropoxylated and/or polyethoxylated or both. Suitable anionic surfactants may include alkali metal alkyl sulfates, alkyl ether sulfonates, alkyl sulfonates, alkyl aryl sulfonates, linear and branched alkyl ether sulfates and sulfonates, alcohol polypropoxylated sulfates, alcohol polyethoxylated sulfates, alcohol polypropoxylated polyethoxylated sulfates, alkyl disulfonates, alkylaryl disulfonates, alkyl disulfates, alkyl sulfosuccinates, alkyl ether sulfates, linear and branched ether sulfates, alkali metal carboxylates, fatty acid carboxylates, and phosphate esters. Suitable cationic surfactants may include, but are not necessarily limited to, arginine methyl esters, alkanolamines and alkylenediamides. Suitable surfactants may also include surfactants containing a non-ionic spacer-arm central extension and an ionic or nonionic polar group. Other suitable surfactants may be dimeric or gemini surfactants, cleavable surfactants, janus surfactants and extended surfactants, also called extended chain surfactants.

In the foregoing specification, the invention has been described with reference to specific embodiments thereof, and has been described as effective in providing methods and compositions for detecting a spin probe within an oilfield fluid or probing an oilfield fluid for particular properties. However, it will be evident that various modifications and changes can be made thereto without departing from the broader spirit or scope of the invention as set forth in the appended claims. Accordingly, the specification is to be regarded in an illustrative rather than a restrictive sense. For example, specific oilfield fluids, spin probes, chemicals, and g values of the spin probes falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the method may consist of or consist essentially of detecting at least one spin probe within its microenvironment of an oilfield fluid, such as but not necessarily limited to a drilling fluid, a completion fluid, a production fluid, a servicing fluid, and combinations thereof, where the presence of the spin probe(s) indicates the presence of at least one chemical, pH of the microenvironment, dielectric constant of the microenvironment, rotational freedom of the spin probe(s), the concentration of the chemical(s), residue of the chemical(s) in the fluid, the speciation of the coupled chemistry between the spin probe(s) and the chemical(s), the placement origin of the chemical(s), secondary phenomena of the microenvironment, and combinations thereof.

In another embodiment, there may be a fluid composition consisting of or consisting essentially of an oilfield fluid selected from the group consisting of a drilling fluid, a completion fluid, a production fluid, a servicing fluid, and combinations thereof; at least one spin probe; and at least one chemical selected from the group consisting of asphaltene inhibitors, paraffin inhibitors, scale inhibitors, corrosion inhibitors, biocides, hydrate inhibitors, oxygen scavengers, hydrogen sulfide scavengers, demulsifiers, reverse emulsion breakers, water clarifiers, drag reducers, foamers, defoamers, fracturing fluid additives, and combinations thereof.

The words "comprising" and "comprises" as used throughout the claims, are to be interpreted to mean "including but not limited to" and "includes but not limited to", respectively.

What is claimed is:

1. A method comprising:
   detecting at least one spin probe within its microenvironment of an oilfield fluid, wherein the presence of the at least one spin probe indicates the presence of at least one chemical, pH of the microenvironment, dielectric constant of the microenvironment, rotational freedom of the at least one spin probe, the concentration of the at least one chemical, residue of the at least one chemical in the fluid, the speciation of the coupled chemistry between the at least one spin probe and the at least one chemical, the placement origin of the at least one chemical, secondary phenomena of the microenvironment, and combinations thereof; wherein the oilfield fluid is selected from the group consisting of a drilling fluid, a completion fluid, a production fluid, a servicing fluid, and combinations thereof; wherein the concentration of the at least one spin probe within the oilfield fluid ranges from about 10 ppm to about 50,000 ppm; and
   where the at least one spin probe was added to the oilfield fluid prior to detecting the at least one spin probe, and wherein the at least one spin probe is attached to the at least one chemical wherein the attachment of the at least one spin probe to the at least one chemical is a covalent attachment via a reaction selected from the group consisting of esterification, nucleophilic addition, substitution, elimination, rearrangement, and combinations thereof.

2. The method of claim 1, wherein the at least one chemical is selected from the group consisting of an oil-based chemical, a water-based chemical, and combinations thereof.

3. The method of claim 1, wherein the at least one spin probe is selected from the group consisting of [(2,2,6,6-tetramethylpiperidin-1-yl)oxyl](TEMPO); [2,2,5,5-tetramethylpyrrolidin-1-yloxyl] (Proxyl); [2,2,5,5-tetramethyl-3-oxazolidinoxy] (Doxo); [2,2,5,5tetramethyl-1-dihydropyrrolinoxy](Proxo); [2,2,3,4,5,5-hexamethyl-imidazoline-1yloxyl] (Imidazo); [2,5-dihydro-3-(hydroxymethyl)-2,2,5,5-tetramethyl-1H-pyrrol-1-yloxy]; [5-(Diethoxyphosphoryl)-5-methyl-1-pyrroline-N-oxide] (DEPMPO); [5-(Diisopropoxyphosphoryl)-5-methyl-1-pyrroline-N-oxide]; [2-Diisopropylphosphono-2-methyl-3,4-dihydro-2H-pyrrole-1-oxide] (DIPPMPO); [5-tert-Butoxycarbonyl-5-methyl-1-pyrroline-N-oxide] (BMPO); [5,5-Dimethyl-1-pyrroline-N-oxide] (DMPO); [2-Ethoxycarbonyl-2-methyl-3,4-dihydro-2H-pyrrole-1-oxide] (EMPO); [4-Hydroxy-5,5-dimethyl-2-trifluoromethylpyrroline-1-oxide] (FDMPO); [bis-(2,2,5,5-Tetramethyl-3-imidazoline-1-oxyl-4-yl) disulfide, biradical] (RSSR); [4-(Dimethylamino)-2-ethyl-5,5-dimethyl-2-pyridine-4-yl-2,5-dihydro-1H-imidazol-1-oxyl] (DEDPI); [(1-Oxyl-2,2,5,5-tetramethylpyrroline-3-methyl)] methanethiosulfonate (MTSSL); [2-n-Heptyl-4-hydroxyquinoline N-oxide] (HQNO); [N-t-Butyl-α-phenylnitrone] (PBN); [N-(Dithiocarbamoyl)-N-methyl-D-glucamine (MGD. Na.H2O)];

Diethyldithiocarbamate; [2-(4-Carboxyphenyl)-4,4,5,5-tetramethylimidazoline-1-oxyl-3-oxide. potassium salt] (Carboxy-PTIO.K); transition metal ions, lanthanides metal ions, rare earth metals, salts and complexes thereof; and combinations thereof.

4. The method of claim 1, wherein the amount of the at least one chemical in the oilfield fluid ranges from about 10 ppm to about 20,000 ppm.

5. The method of claim 1, wherein the at least one chemical is selected from the group consisting of asphaltene inhibitors, paraffin inhibitors, scale inhibitors, corrosion inhibitors, biocides, low dose hydrate inhibitors, oxygen scavengers, hydrogen sulfide scavengers, demulsifiers, reverse emulsion breakers, water clarifiers, drag reducers, foamers, defoamers, fracturing fluid additives, water flooding additives, carbon dioxide flooding additives, and combinations thereof, and combinations thereof.

6. A method for probing an oilfield fluid for at least one spin probe attached to at least one chemical, wherein the method comprises:
adding the at least one spin probe attached to the at least one chemical to the oilfield fluid; wherein the attachment of the at least one spin probe to the at least one chemical is a covalent attachment via a reaction selected from the group consisting of esterification, nucleophilic addition, substitution, elimination, rearrangement, and combinations thereof;
detecting the at least one spin probe attached to the at least one chemical within an oilfield fluid selected from the group consisting of a drilling fluid, a completion fluid, a production fluid, a servicing fluid, and combinations thereof; and wherein the at least one chemical is selected from the group consisting of an oil-based chemical, a water-based chemical, and combinations thereof; and
wherein the detecting the at least one spin probe within its microenvironment indicates the at least one chemical, pH of the microenvironment, dielectric constant of the microenvironment, rotational freedom of the spin probe, the concentration of the at least one chemical, residue of at least one chemical in the oilfield fluid, the speciation of the coupled chemistry between the spin probe and the chemical, the placement origin of the at least one chemical, secondary phenomena of the microenvironment, and combinations thereof.

7. The method of claim 6, further comprising detecting an amount of the at least one spin probe within the oilfield fluid, wherein the amount of the at least one spin probe ranges from about 10 ppm to about 50,000 ppm.

8. The method of claim 6, wherein the at least one spin probe is selected from the group consisting of [(2,2,6,6-tetramethylpiperidin-1-yl)oxyl] (TEMPO); [2,2,5,5-tetramethylpyrrolidin-1-yloxyl] (Proxyl); [2,2,5,5-tetramethyl-3-oxazolidinoxy] (Doxo); [2,2,5,5tetramethyl-1-dihydropyrrolinoxy] (Proxo); [2,2,3,4,5,5-hexamethyl-imidazoline-1yloxyl] (Imidazo); [2,5-dihydro-3-(hydroxymethyl)-2,2,5,5-tetramethyl-1H-pyrrol-1-yloxy]; [5-(Diethoxyphosphoryl)-5-methyl-1-pyrroline-N-oxide] (DEPMPO); [5-(Diisopropoxyphosphoryl)-5-methyl-1-pyrroline-N-oxide]; [2-Diisopropylphosphono-2-methyl-3,4-dihydro-2H-pyrrole-1-oxide] (DIPPMPO); [5-tert-Butoxycarbonyl-5-methyl-1-pyrroline-N-oxide] (BMPO); [5,5-Dimethyl-1-pyrroline-N-oxide] (DMPO); [2-Ethoxycarbonyl-2-methyl-3,4-dihydro-2H-pyrrole-1-oxide] (EMPO); [4-Hydroxy-5,5-dimethyl-2-trifluoromethylpyrroline-1-oxide] (FDMPO); [bis-(2,2,5,5-Tetramethyl-3-imidazoline-1-oxyl-4-yl) disulfide, biradical] (RSSR); [4-(Dimethylamino)-2-ethyl-5,5-dimethyl-2-pyridine-4-yl-2,5-dihydro-1H-imidazol-1-oxyl] (DEDPI); [(1-Oxyl-2,2,5,5-tetramethylpyrroline-3-methyl)] methanethiosulfonate (MTSSL); [2-n-Heptyl-4-hydroxyquinoline N-oxide] (HQNO); [N-t-Butyl-α-phenylnitrone] (PBN); [N-(Dithiocarbamoyl)-N-methyl-D-glucamine (MGD.Na.H2O)]; Diethyldithiocarbamate; [2-(4-Carboxyphenyl)-4,4,5,5-tetramethylimidazoline-1-oxyl-3-oxide. potassium salt] (Carboxy-PTIO.K); transition metal ions, lanthanides metal ions, rare earth metals, salts and complexes thereof; and combinations thereof.

9. The method of claim 6, wherein the at least one spin probe has a g value ranging from about 1.4 to about 3.0.

10. A method comprising: detecting at least one spin probe within its microenvironment of an oilfield fluid, wherein the presence of the at least one spin probe indicates the presence of at least one chemical, pH of the microenvironment, dielectric constant of the microenvironment, rotational freedom of the at least one spin probe, the concentration of the at least one chemical, residue of the at least one chemical in the fluid, the speciation of the coupled chemistry between the at least one spin probe and the at least one chemical, the placement origin of the at least one chemical, secondary phenomena of the microenvironment, and combinations thereof; wherein the oilfield fluid is selected from the group consisting of a drilling fluid, a completion fluid, a production fluid, a servicing fluid, and combinations thereof; wherein the at least one spin probe is selected from the group consisting of [(2,2,6,6-tetramethylpiperidin-1-yl)oxyl] (TEMPO); [2,2,5,5-tetramethylpyrrolidin-1-yloxyl] (Proxyl); [2,2,5,5-tetramethyl-3-oxazolidinoxy] (Doxo); [2,2,5,5tetramethyl-1-dihydropyrrolinoxy] (Proxo); [2,2,3,4,5,5-hexamethyl-imidazoline-1yloxyl] (Imidazo); [2,5-dihydro-3-(hydroxymethyl)-2,2,5,5-tetramethyl-1H-pyrrol-1-yloxy]; [5-(Diethoxyphosphoryl)-5-methyl-1-pyrroline-N-oxide] (DEPMPO); [5-(Diisopropoxyphosphoryl)-5-methyl-1-pyrroline-N-oxide]; [2-Diisopropylphosphono-2-methyl-3,4-dihydro-2H-pyrrole-1-oxide] (DIPPMPO); [5-tert-Butoxycarbonyl-5-methyl-1-pyrroline-N-oxide](BMPO); [5,5-Dimethyl-1-pyrroline-N-oxide] (DMPO); [2-Ethoxycarbonyl-2-methyl-3,4-dihydro-2H-pyrrole-1-oxide] (EMPO); [4-Hydroxy-5,5-dimethyl-2-trifluoromethylpyrroline-1-oxide] (FDMPO); [bis-(2,2,5,5-Tetramethyl-3-imidazoline-1-oxyl-4-yl) disulfide, biradical] (RSSR); [4-(Dimethylamino)-2-ethyl-5,5-dimethyl-2-pyridine-4-yl-2,5-dihydro-1H-imidazol-1-oxyl] (DEDPI); [(1-Oxyl-2,2,5,5-tetramethylpyrroline-3-methyl)] methanethiosulfonate (MTSSL); [2-n-Heptyl-4-hydroxyquinoline N-oxide](HQNO); [N-t-Butyl-α-phenylnitrone] (PBN); [N-(Dithiocarbamoyl)-N-methyl-D-glucamine (MGD.Na.H$_2$O)]; Diethyldithiocarbamate; [2-(4-Carboxyphenyl)-4,4,5,5-tetramethylimidazoline-1-oxyl-3-oxide. potassium salt] (Carboxy-PTIO.K); transition metal ions, lanthanides metal ions, rare earth metals, salts and complexes thereof; and combinations thereof.

* * * * *